United States Patent
Xi et al.

(10) Patent No.: US 9,695,150 B2
(45) Date of Patent: *Jul. 4, 2017

(54) CRYSTALLINE FORM OF A SUBSTITUTED QUINOLINE COMPOUND AND PHARMACEUTICAL COMPOSITIONS THEREOF

(71) Applicants: Sunshine Lake Pharma Co., Ltd., Dongguan, Guangdong (CN); Calitor Sciences, LLC, Newbury, CA (US)

(72) Inventors: Ning Xi, Newbury Park, CA (US); Mingming Sun, Guangdong (CN)

(73) Assignees: CALITOR SCIENCES, LLC, Newbury Park, CA (US); SUNSHINE LAKE PHARMA CO., LTD., Dongguan, Guangdong (CN)

(*) Notice: Subject to any disclaimer, the term of this patent is extended or adjusted under 35 U.S.C. 154(b) by 0 days.

This patent is subject to a terminal disclaimer.

(21) Appl. No.: 15/350,014

(22) Filed: Nov. 12, 2016

(65) Prior Publication Data

US 2017/0137404 A1    May 18, 2017

Related U.S. Application Data

(60) Provisional application No. 62/255,392, filed on Nov. 14, 2015.

(51) Int. Cl.
| | | |
|---|---|---|
| *A61K 31/436* | (2006.01) | |
| *A61K 31/4709* | (2006.01) | |
| *A61K 45/06* | (2006.01) | |
| *A61K 38/21* | (2006.01) | |
| *C07D 401/12* | (2006.01) | |
| *A61K 9/48* | (2006.01) | |
| *A61K 9/00* | (2006.01) | |

(52) U.S. Cl.
CPC .......... *C07D 401/12* (2013.01); *A61K 9/0053* (2013.01); *A61K 9/48* (2013.01); *A61K 31/436* (2013.01); *A61K 31/4709* (2013.01); *A61K 38/21* (2013.01); *A61K 45/06* (2013.01); *C07B 2200/13* (2013.01)

(58) Field of Classification Search
CPC .. A61K 31/436; A61K 31/4709; A61K 38/21; A61K 45/06; C07D 401/12
See application file for complete search history.

(56) References Cited

U.S. PATENT DOCUMENTS

| | | |
|---|---|---|
| 9,133,162 B2 | 9/2015 | Xi |
| 2015/0342945 A1 | 12/2015 | Xi |

*Primary Examiner* — Yong Chong
(74) *Attorney, Agent, or Firm* — Kam W. Law; Squire Patton Boggs (US) LLP (57) ABSTRACT

The present invention relates to a crystalline form of N-(3-fluoro-4-((7-(2-hydroxy-2-methylpropoxy)quinolin-4-yl)oxy)phenyl)-1,5-dimethyl-3-oxo-2-phenyl-2,3-dihydro-1H-pyrazole-4-carboxamide p-toluenesulfonate, the process for preparing the crystalline form thereof, and pharmaceutical compositions comprising the crystalline form thereof. This invention also relates to a method of using such a crystalline form in the treatment of hyperproliferative diseases in mammals, especially in humans.

7 Claims, 3 Drawing Sheets

CRYSTALLINE FORM OF A SUBSTITUTED QUINOLINE COMPOUND AND PHARMACEUTICAL COMPOSITIONS THEREOF

CROSS-REFERENCE TO RELATED APPLICATIONS

This application claims the benefit of U.S. Provisional Application No. 62/255,392, filed on Nov. 14, 2015, which is hereby incorporated by reference in its entirety.

FIELD OF THE INVENTION

This invention relates to a crystalline form of N-(3-fluoro-4-((7-(2-hydroxy-2-methylpropoxy)quinolin-4-yl)oxy)phenyl)-1,5-dimethyl-3-oxo-2-phenyl-2,3-dihydro-1H-pyrazole-4-carboxamide p-toluenesulfonate, the process for preparing the crystalline form thereof, and pharmaceutical compositions comprising the crystalline form, and pharmaceutical compositions comprising the crystalline form thereof. This invention also relates to a method of using such a crystalline form in the treatment of hyperproliferative diseases in mammals, especially in humans.

BACKGROUND OF THE INVENTION

Traditionally, dramatic improvements in the treatment of cancer are associated with identification of therapeutic agents acting through novel mechanisms. One mechanism that has been exploited in cancer treatment is the modulation of protein kinase activity, because signal transduction through protein kinase activation is responsible for many of the characteristics of tumor cells. Protein kinase signal transduction is of particular relevance in, for example, thyroid, gastric, kidney, brain, head and neck, lung, breast, prostate and colorectal cancers, as well as in the growth and proliferation of brain tumor cells, among many other solid and blood cancers.

Protein kinases can be categorized as receptor type or non-receptor type. Receptor-type tyrosine kinases generally comprise of a transmenbrane receptors with diverse biological activities. For a detailed discussion of the receptor-type tyrosine kinases, see "Structural biology of protein tyrosine kinases", *Cell. Mol. Life Sci.*, 2006 (63), 2608-2625. Since kinases and their ligands play critical roles in various cellular activities, dysregulation of protein kinase activity can lead to altered cellular properties, such as uncontrolled cell growth associated with cancer. Therefore, protein kinases are attractive targets for small molecule drug discovery. Particularly attractive targets for small-molecule modulation with respect to antiangiogenic and antiproliferative activity include receptor tyrosine kinases such as VEGFRs, Flt3, c-Met, Axl and Mer, among many others.

Angiogenesis, the formation of new capillaries from pre-existing blood vessels, is a necessary process for organ development during embryogenesis and is critical for the female reproductive cycle, inflammation, and wound healing in the adult. Certain diseases are known to be associated with dysregulated angiogenesis, for example ocular neovascularization, such as retinopathies (including diabetic retinopathy), age-related macular degeneration, fibrosis, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias). Solid tumors, in particular, are dependent on angiogenesis to grow beyond a certain critical size by inducing new capillaries sprouting from existing blood vessels to secure their nutrition, oxygen supply, and waste removal. In addition, angiogenesis also promotes metastasis of tumor cells to other sites.

The new vessel growth and maturation are highly complex and coordinated processes, requiring the stimulation by a number of growth factors. Vascular endothelial growth factor (VEGF) signaling often represents a critical rate-limiting step in physiological and pathological angiogenesis. VEGF binds to and activates the receptor tyrosine kinase, VEGFR. Three VEGFR isoforms have been identified in humans: VEGFR-1 (Flt-1), VEGFR-2 (KDR/Flk-1) and VEGFR-3 (Flt-4). VEGFR-2 mediates the majority of cellular responses to VEGF, in particular its mitogenic and angiogenic effects. VEGFR-1 is thought to modulate VEGFR-2 signaling or to act as a dummy/decoy receptor to sequester VEGF away from VEGFR-2. (Stuttfeld E, Ballmer-Hofer K (2009). "Structure and function of VEGF receptors". *IUBMB Life* 61 (9): 915-22.)

Since VEGFR-2 is the major mediator of vascular endothelial cell (EC) mitogenesis and survival, as well as angiogenesis and microvascular permeability, it is expected that direct inhibition of the kinase activity of VEGFR-2 will result in the reduction of angiogenesis and the suppression of tumor growth. Furthermore, inhibition of VEGFR-2 targeting the genetically more stable host endothelial cells, instead of labile tumor tissues, may decrease the chance of resistance development. Several agents targeting VEGFR signaling, administered either as single agents or in combination with chemotherapy, have been shown to benefit patients with advanced-stage malignancies. ("VEGF-targeted therapy: mechanisms of anti-tumor activity." *Nature Reviews Cancer*, 2008, 8, 579; "Molecular basis for sunitinib efficacy and future clinical development." *Nature Reviews Drug Discovery*, 2007, 6, 734; "Angiogenesis: an organizing principle for drug discovery?" *Nature Reviews Drug Discovery*, 2007, 6, 273).

FLT3 (Flt3, FMS-related tyrosine kinase 3), also known as FLK-2 (fetal liver kinase 2) and STK-1 (human stem cell kinase 1), belongs to a member of the class III receptor tyrosine kinase (RTK-III) family that include KIT, PDGFR, FMS and FLT1 (Stirewalt D L, et al., *Nat. Rev Cancer*, 2003, 3:650-665). FLT3 has been implicated in hematopoietic disorders which are pre-malignant disorders including myeloproliferative disorders, such as thrombocythemia, essential thrombocytosis (ET), myelofibrosis (MF), chronic idiopathic myelofibrosis (LMF), and polycythemia vera (PV), pre-malignant myelodysplastic syndromes. Hematological malignancies include leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL) (Matthew C. Stubbs and Scott A. Armstrong, "FLT3 as a Therapeutic Target in Childhood Acute Leukemia." *Current Drug Targets*, 2007, 8, 703-714).

FLT3 is overexpressed at the levels in 70-100% of cases of acute myeloid leukemias (AML), and in a high percentage of T-acute lymphocytic leukemia (ALL) cases (Griffin J D, et al., *Haematol J.* 2004, 5: 188-190). It is also overexpressed in a smaller subset of chronic myeloid leukemia (CML) in blast crisis. Studies have shown that the leukemic cells of B lineage ALL and AML frequently co-express FL, setting up autocrine or paracrine signaling loops that result in the constitutive activation of FLT3 (Zheng R, et. al., *Blood.*, 2004, 103: 267-274). A high level of the FLT3 ligand is found in the serum of patients with Langerhans cell histocytosis and systemic lupus erythematosus, which further implicates FLT3 signaling in the dysregulation of dendritic cell progenitors in those autoimmune diseases (Rolland et al., *J. Immunol.*, 2005, 174:3067-3071; Engen et al., "Targeted Therapy of FLT3 in Treatment of AML—Current Status and Future Directions." *J. Clin. Med.*, 2014, 3, 1466-1489).

c-Met, also referred to as hepatocyte growth factor receptor (HGFR), is expressed predominantly in epithelial cells but has also been identified in endothelial cells, myoblasts, hematopoietic cells and motor neurons. The natural ligand for c-Met is hepatocyte growth factor (HGF), also known as scatter factor (SF). In both embryos and adults, activated c-Met promotes a morphogenetic program, known as invasive growth, which induces cell spreading, the disruption of intercellular contacts, and the migration of cells towards their surroundings. ("From Tpr-Met to Met, tumorigenesis and tubes." *Oncogene*, 2007, 26, 1276; "Met Receptor Tyrosine Kinase as a Therapeutic Anticancer Target." *Cancer Letter*, 2009, 280, 1-14).

A wide variety of human malignancies exhibit sustained c-Met stimulation, overexpression, or mutation, including carcinomas of the breast, liver, lung, ovary, kidney, thyroid, colon, renal, glioblastomas, and prostate, etc. c-Met is also implicated in atherosclerosis and organ fibrosis such as lung fibrosis. Invasive growth of certain cancer cells is drastically enhanced by tumor-stromal interactions involving the HGF/c-Met pathway. Thus, extensive evidence that c-Met signaling is involved in the progression and spread of several cancers has generated considerable interest in c-Met as major targets in cancer drug development. ("Molecular cancer therapy: can our expectation be MET." *Euro. J. Cancer*, 2008, 44, 641-651; "Targeting the c-Met Signaling Pathway in Cancer." *Clin. Cancer Res.*, 2006, 12, 3657). Agents targeting c-Met signaling pathway are now under clinical investigation. ("Novel Therapeutic Inhibitors of the c-Met Signaling Pathway in Cancer." *Clinical Cancer Research*, 2009, 15, 2207; "Drug development of MET inhibitors: targeting oncogene addiction and expedience." *Nature Review Drug Discovery*, 2008, 7, 504).

The TYRO3, AXL (also known as UFO) and MERTK (also known as Mer) (TAM) family of receptor tyrosine kinases (RTKs) was one of the latest to evolve. Members of this family have a similar overall domain structure and are highly related by a unique KWIAIES conserved sequence in their kinase domain. TAM RTKs are ectopically expressed or overexpressed in a wide variety of human cancers in which they provide tumor cells with a survival advantage. In experimental models, Axl and MerTK can be oncogenic. Although MerTK and Axl can activate standard proliferative pathways (ERK, AKT and members of the signal transducer and activator of transcription (STAT) family), their output generally promotes survival rather than proliferation. These kinases are potentially dual anticancer targets, firstly in tumor cells that have developed a non-oncogene addiction to TAM RTK survival signals and secondly in the microenvironment where MerTK and Axl inhibition may reverse innate immune suppression. ("The TAM family: phosphatidylserine-sensing receptor tyrosine kinases gone awry in cancer." *Nature Review Cancer*, 2014, 14, 769)

Recently a study showed that Mer and Axl were frequently overexpressed and activated in many tumor cell lines, such as in various NSCLC cell lines. Ligand-dependent Mer or Axl activation stimulated MAPK, AKT and FAK signaling pathways indicating roles for these RTKs in multiple oncogenic processes. Abnormal expression and activation of Axl knockdown also improved in vitro NSCLC sensitivity to chemotherapeutic agents by promoting apoptosis. When comparing the effects of Mer and Axl knockdown, Mer inhibition exhibited more complete blockade of tumor growth while Axl knockdown more robustly improved chemosensitivity. Therefore, inhibition of Axl, Mer or both is potentially a therapeutic strategy to target cancer cells (Rachel et al., "Mer or Axl Receptor Tyrosine Kinase inhibition promotes apoptosis, blocks growth, and enhances chemosensitivity of human non-small cell lung cancer" *Oncogene*, 2013, 32(29), 3420-3431).

Accordingly, small-molecule compounds that specially inhibit, regulate and/or modulate the signal transduction of kinases, particularly including VEGFRs, Flt3, c-Met, Axl and Mer as described above, are desirable as a means to treat or prevent disease states associated with abnormal cell proliferation and angiogenesis. One such small-molecule is N-(3-fluoro-4-((7-(2-hydroxy-2-methylpropoxy)quinolin-4-yl)oxy)phenyl)-1,5-dimethyl-3-oxo-2-phenyl-2,3-dihydro-1H-pyrazole-4-carboxamide, which has the chemical structure as shown in the following:

WO 2012118632 A1 described the synthesis of N-(3-fluoro-4-((7-(2-hydroxy-2-methylpropoxy)quinolin-4-yl)oxy)phenyl)-1,5-dimethyl-3-oxo-2-phenyl-2,3-dihydro-1H-pyrazole-4-carboxamide (Example 1), the salts thereof, such as hydrochloride (Example 5), maleate (Example 6), p-toluenesulfonate (Example 7), and benzene sulfonate (Example 8), and also disclosed the therapeutic activity of these molecules and salts thereof in inhibiting, regulating and modulating the signal transduction of protein kinases.

Different salts and solid state form of an active pharmaceutical ingredient may possess different properties. Such variations in the properties of different salts and solid state forms may provide a basis for improving formulation, for example, by facilitating better processing or handling characteristics, improving the dissolution profile, stability (polymorph as well as chemical stability) and shelf-life. These variations in the properties of different salts and solid state forms may also provide improvements to the final dosage form, for example, if they serve to improve bioavailability. Different salts and solid state forms of an active pharmaceutical ingredient may also give rise to a variety of polymorphs or crystalline forms, which may in turn provide additional opportunities to assess variations in the properties and characteristics of a solid active pharmaceutical ingredient.

SUMMARY OF THE INVENTION

The present invention provides a crystalline form of N-(3-fluoro-4-((7-(2-hydroxy-2-methylpropoxy)quinolin-4-yl)oxy)phenyl)-1,5-dimethyl-3-oxo-2-phenyl-2,3-dihydro-1H-pyrazole-4-carboxamide p-toluenesulfonate, and novel pharmaceutical compositions containing the crystalline form thereof. The invention also encompasses the therapeutic uses of the crystalline form described herein and the therapeutic compositions containing the crystalline form described herein. The techniques used to characterize the crystalline form are described in the examples herein. These techniques, alone or in combination, may be used to characterize the crystalline form disclosed herein. The crystalline form may be also characterized by reference to the figures disclosed herein.

In one aspect, provided herein is a crystalline form of the compound of formula (I):

(I)

wherein the crystalline form is form C having:
a) an X-ray powder diffraction pattern comprising peaks, in terms of 2θ, at about 7.20°, about 10.06°, about 17.40°, about 17.75°, about 18.65°, about 19.48° and about 20.13°; or
b) an X-ray powder diffraction pattern comprising peaks, in terms of 2θ, at 7.20°±0.2°, 10.06°±0.2°, 17.40°±0.2°, 17.75°±0.2°, 18.65°±0.2°, 19.48°±0.2° and 20.13°±0.2°.

In one embodiment, the crystalline form C has an X-ray powder diffraction pattern comprising peaks, in terms of 2θ, at about 7.20°, about 10.06°, about 14.96°, about 16.76°, about 17.40°, about 17.75°, about 18.65°, about 19.48°, about 20.13°, about 20.90°, about 21.71°, about 22.69°, about 23.37°, about 24.40°, about 25.52°, about 26.29° and about 28.41°; or at 7.200±0.2°, 10.06°±0.2°, 14.96±0.2°, 16.76±0.2°, 17.40°±0.2°, 17.75°±0.2°, 18.65°±0.2°, 19.48°±0.2°, 20.13°±0.2°, 20.90°±0.2°, 21.71°±0.2°, 22.69°±0.2°, 23.37°±0.2°, 24.40°±0.2°, 25.52°±0.2°, 26.29°±0.2° and 28.41°±0.2°.

Figure 1:
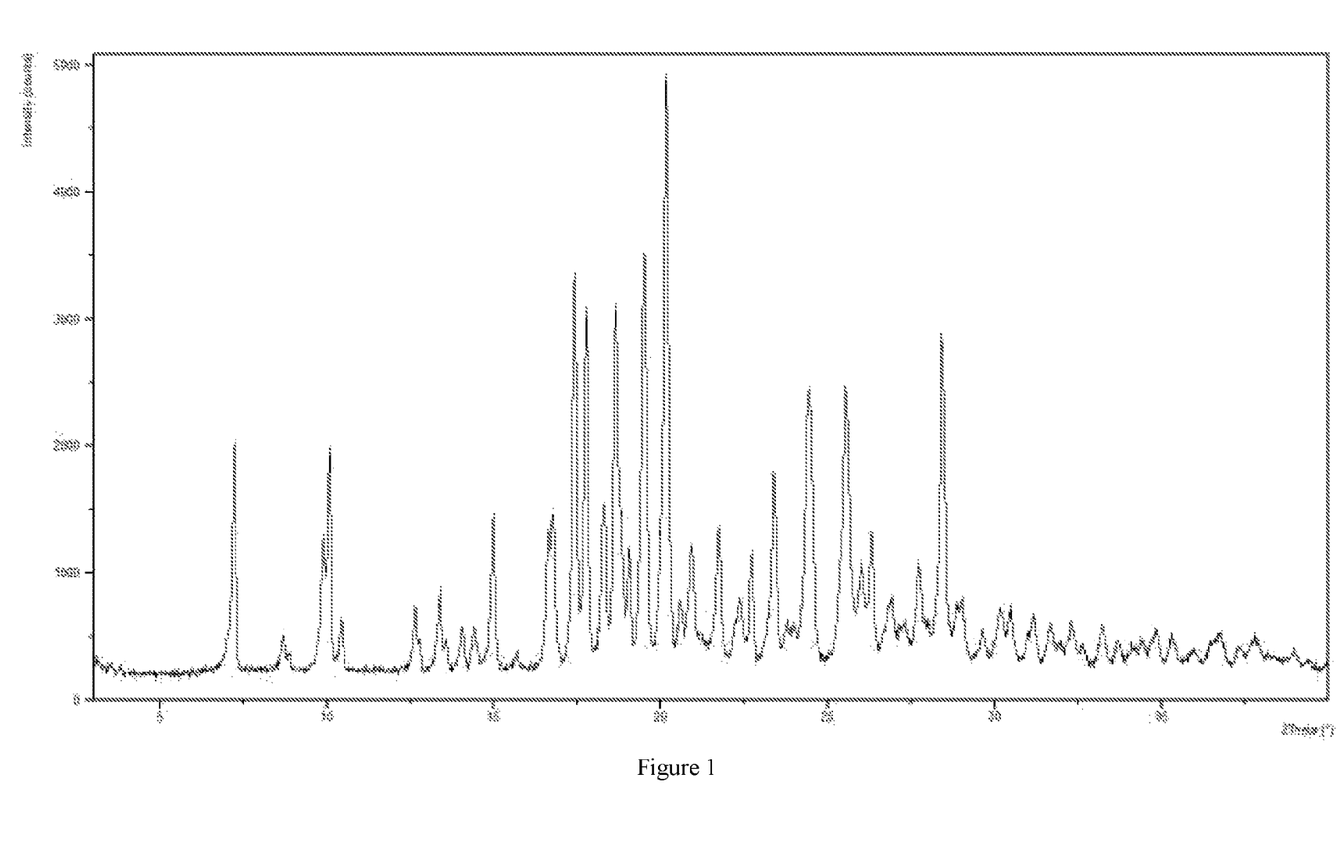
FIG. 1 depicts an X-ray powder diffraction pattern of the crystalline form C of compound (I).

In another embodiment, the crystalline form C has an X-ray powder diffraction pattern is substantially in accordance with that shown in FIG. 1.

In one embodiment, the crystalline form C has a differential scanning calorimetry trace comprising two endothermic peaks at 168° C.±3° C. and 219° C.±3° C.

Figure 2:
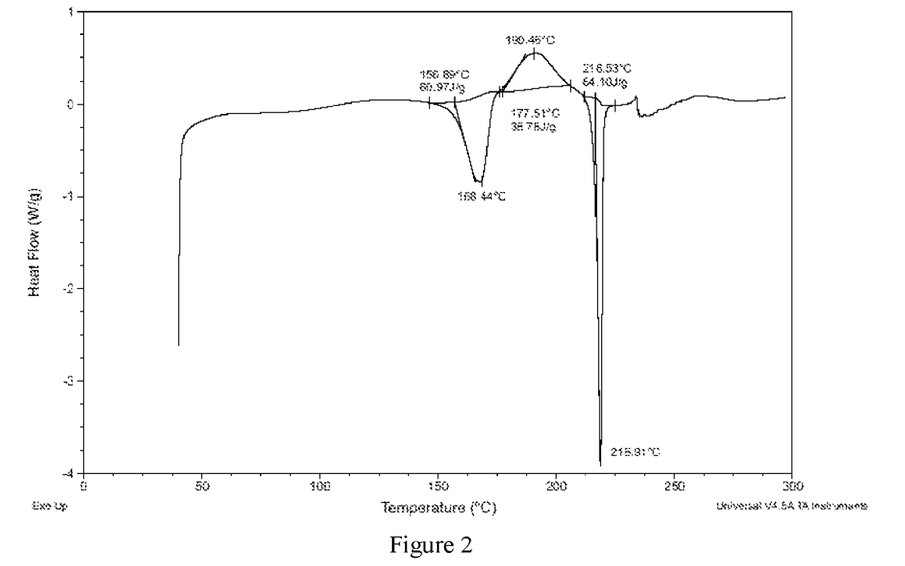
FIG. 2 depicts a differential scanning calorimetry thermogram of the crystalline form C of compound (I).

In another embodiment, the crystalline form C has a differential scanning calorimetry trace substantially in accordance with that shown in FIG. 2.

In one embodiment, the crystalline form C has a thermal gravimetric analysis curve comprising a weight loss of about 3.5% when heated to about 185° C.

Figure 3:
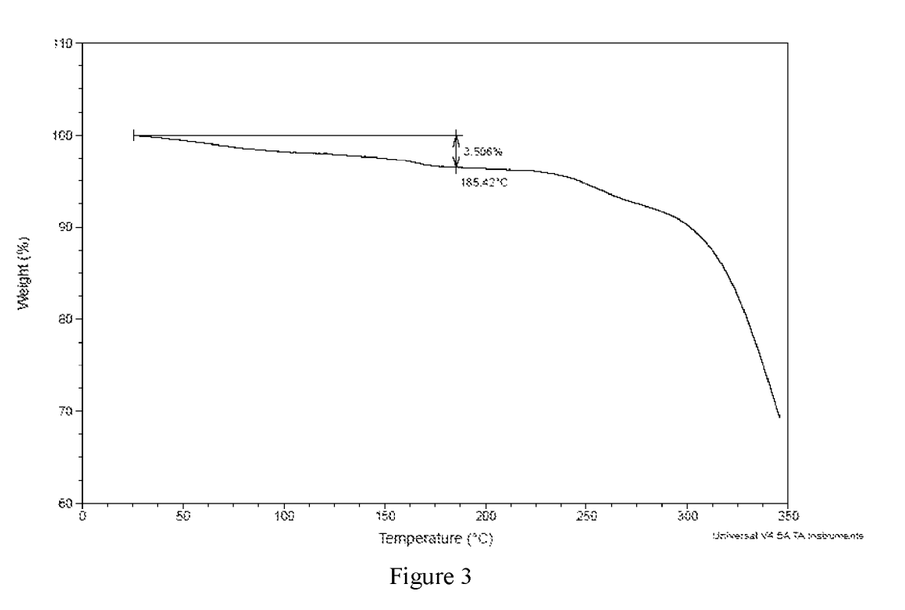
FIG. 3 depicts a thermal gravimetric analysis curve of the crystalline form C of compound (I).
Figure 4:
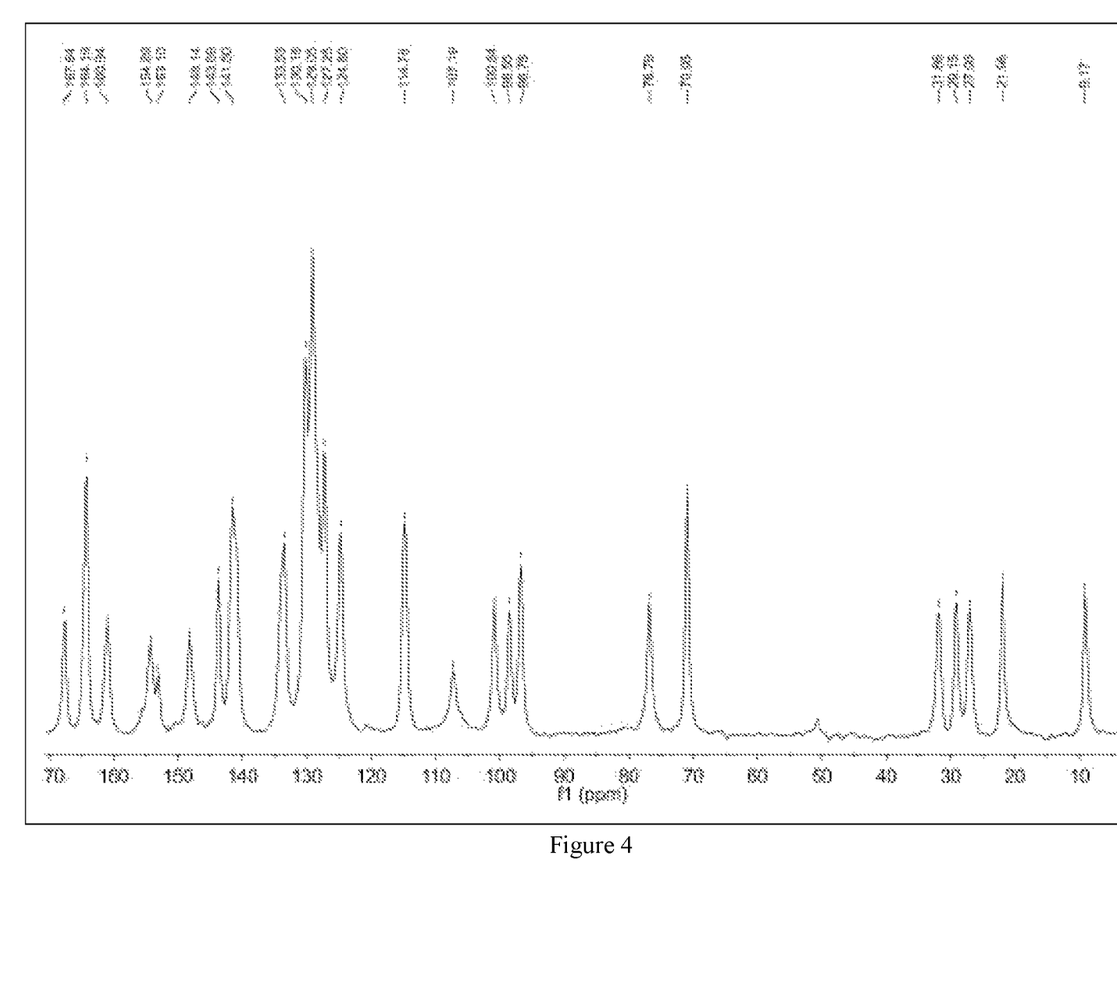
FIG. 4 depicts a solid-state $^{13}C$ NMR spectra of the crystalline form C of compound (I).

In another embodiment, the crystalline form C has a thermal gravimetric analysis curve is substantially in accordance with that shown in FIG. 3.

In another embodiment, the crystalline form is substantially pure.

In another aspect, provided herein is a pharmaceutical composition comprising the crystalline form C.

In one embodiment, the composition further comprises a pharmaceutically acceptable excipient, carrier, vehicle or a combination thereof.

In another embodiment, the pharmaceutical composition further comprises a therapeutic agent, In further embodiments, the therapeutic agent is melphalan, cyclophosphamide, ifosfamide, busulfan, carmustine, lomustine, streptozocin, cisplatin, carboplatin, oxaliplatin, dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, topotecan, irinotecan, etoposide, trabectedin, dactinomycin, doxorubicin, epirubicin, daunorubicin, mitoxantrone, bleomycin, mitomycin, ixabepilone, tamoxifen, flutamide, gonadorelin analogues, megestrol, prednisone, dexamethasone, methylprednisolone, thalidomide, interferon alfa, leucovorin, sirolimus, temsirolimus, everolimus, afatinib, alisertib, amuvatinib, apatinib, axitinib, bosutinib, bortezomib, brivanib, cediranib, cabozantinib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, neratinib, nilotinib, niraparib, oprozomib, olaparib, pazopanib, pegaptanib, pictilisib, ponatinib, quizartinib, radotinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, vemurafenib, vismodegib, volasertib, alemtuzumab, bevacizumab, brentuximabvedotin, catumaxomab, cetuximab, denosumab, gemtuzumab, ipilimumab, nimotuzumab, ofatumumab, panitumumab, ramucirumab, rituximab, tositumomab, trastuzumab, idelalisib, duvelisib, gilteritinib, buparlisib, taselisib, copanlisib, voxtalisib, pilaralisib, sonolisib, perifosine, alectinib, ibrutinib, pertuzumab, nintedanib, cobimetinib, temsirolimus, sirolimus, pixantrone or a combination thereof.

In another aspect, provided herein is a method of preventing, treating or lessening the severity of a proliferative disorder in a patient by administering to the patient with the crystalline form C disclosed herein or the pharmaceutical composition disclosed herein.

In one embodiment, wherein the proliferative disorder is colon cancer, rectal cancer, gastric cancer, gastric adenocarcinoma, pancreatic cancer, bladder cancer, gallbladder cancer, breast cancer, kidney cancer, renal cell carcinoma, liver cancer, hepatocellular carcinoma, lung cancer, skin cancer, melanoma, thyroid cancer, osteosarcomas, soft tissue sarcoma, a cancer of the head and neck, a cancer of the central nervous system, glioma, glioblastomas, ovarian cancer, uterine cancer, endometrial carcinoma, prostate cancer, acute myeloid leukemia or acute lymphoblastic leukemia, or a metastasis thereof.

In another aspect, provided herein is a method of inhibiting a receptor tyrosine kinase with the crystalline form C disclosed herein or the pharmaceutical composition disclosed herein, wherein the receptor tyrosine kinase is VEGFRs, Flt3, c-Met, Axl, Mer or a combination thereof.

In another aspect, provided herein is the use of the crystalline form A or the pharmaceutical composition disclosed herein in preventing, treating or lessening the severity of a proliferative disease in a patient.

In another aspect, provided herein is the use of the crystalline form A or the pharmaceutical composition disclosed herein in inhibiting or modulating a receptor tyrosine kinase, wherein the receptor tyrosine kinase is VEGFRs, Flt3, c-Met, Axl, Mer or a combination thereof.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

Unless defined otherwise, all technical and scientific terms used herein have the same meaning as is commonly understood by one skilled in the art to which this invention belongs. All patents and publications referred to herein are incorporated by reference in their entirety.

The term "comprising" is meant to be open ended, including the indicated component but not excluding other elements.

As used herein, a crystalline form that is "substantially pure" refers to a crystalline form that is substantially free of one or more other crystalline forms, i.e., the crystalline form has a purity of at least about 60%, at least about 70%, at least about 80%, at least about 85%, at least about 90%, at least about 93%, at least about 95%, at least about 98%, at least about 99%, at least about 99.5%, at least about 99.6%, at least about 99.7%, at least about 99.8%, or at least about 99.9%; or the crystalline form has less than 20%, less than 10%, less than 5%, less than 3%, less than 1%, less than 0.5%, less than 0.1%, or less than 0.01% of the one or more other crystalline forms and/or impurities, based on the total volume or weight of the crystalline form and the one or more other crystalline forms and/or impurities.

As used herein, an X-ray powder diffraction (XRPD) pattern or a differential scanning lorimetry (DSC) thermogram that is "substantially the same as shown" in a figure refers to an X-ray powder diffraction (XRPD) pattern, a differential scanning calorimetry (DSC) thermogram or a thermal gravimetric analysis curve (TGA) having at least 50%, at least 60%, at least 70%, at least 80%, at least 90%, at least 95%, or at least 99% of the peaks shown in the figure.

The term "2 theta value" or "2θ" refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific polymorphic form is intended to mean the 2θ values (in degrees) as measured using the X-ray diffraction experimental conditions described herein.

The term "X-ray powder diffraction pattern" or "XPRD pattern" or "XRD pattern" refers to the experimentally observed diffractogram or parameters derived therefrom. Powder X-ray diffraction patterns are characterized by peak position (abscissa) and intensities (ordinate). In the area of X-ray powder diffraction (XRD), relative peak height of XRD pattern depends on many factors related to sample preparation and geometric shapes of the instrument, while peak position is relatively insensitive to experimental details. Therefore, in some embodiments, the crystalline compounds described herein characterized by XRD pattern with some peak positions, have essentially the same characteristics as XRD pattern provided in appended drawings of the present invention. According to the current state of the instrument for the experiment, the error margin in the scattering angle (2θ) of the diffraction peaks is in the range of ±0.1°, ±0.2°, ±0.3°, ±0.40°, or ±0.5°. In some embodiments, the error margin is ±0.2°.

In the area of differential scanning calorimetry (DSC), relative peak height of DSC trace depends on many factors related to sample preparation and geometric shapes of the instrument, while peak position is relatively insensitive to experiment details. Therefore, in some embodiments, the crystalline compounds disclosed herein characterized by DSC trace with some peak positions, have essentially the same characteristics as DSC trace provided in appended drawings of the present invention. According to the current state of the instrument for the experiment, the error margin in the melting peaks is in the range of ±1° C., ±2° C., ±3° C., ±4° C., or ±5° C. In some embodiments, the error margin is ±3° C.

The term "relative intensity" refers to the intensity of a peak with respect to the intensity of the strongest peak in the X-ray powder diffraction pattern which is regarded as 100%.

As used herein, when referring to a spectrum and/or to data presented in a graph, the term "peak" refers to a feature that one skilled in the art would recognize as not attributable to background noise.

As used herein, all numbers disclosed herein are approximate values, regardless whether the word "about" is used in connection therewith. The value of each number may differ by 1%, 2%, 3%, 4%, 5%, 6%, 7%, 8%, 9%, 10%, 15% or 20%.

General Preparation Methods and Description of Crystalline Form C of Compound (I)

Crystalline forms may be prepared by a variety of methods including, but not limited to, for example, crystallization or recrystallization from a suitable solvent mixture; sublimation; growth from a melt; solid state transformation from another phase; crystallization from a supercritical fluid; and jet spraying. Techniques for crystallization or recrystallization of crystalline forms in a solvent mixture include, but are not limited to, for example, evaporation of the solvent; decreasing the temperature of the solvent mixture; crystal seeding of a supersaturated solvent mixture of the compound and/or salt thereof; freeze drying the solvent mixture; and adding anti-solvents (counter solvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, 2nd Edition, SSCI, West Lafayette, Ind. (1999).

In a crystallization technique in which a solvent or solvents are employed, the solvent(s) are typically chosen based on one or more factors including, but not limited to, for example, solubility of the compound; crystallization technique utilized; and vapor pressure of the solvent. Combinations of solvents may be employed. For example, the compound may be solubilized in a first solvent to afford a solution, to which anti-solvent is then added to decrease the solubility of the compound in the solution, and precipitate to form crystals. An anti-solvent is a solvent in which a compound has low solubility.

Seed crystals may be added to any crystallization mixture to promote crystallization. Seeding may be employed to control growth of a particular polymorph and/or to control the particle size distribution of the crystalline product. Accordingly, calculation of the amount of seeds needed depends on the size of the seed available and the desired size of an average product particle as described, for example, in "Programmed Cooling Batch Crystallizers", J. W. Mullin and J. Nyvlt, *Chemical Engineering Science*, 1971, 26, 369-377. In general, seeds of small particle size are needed to effectively control the growth of crystals in the batch. Seeds of small particle size may be generated by sieving, milling or micronizing large crystals, or by microcrystallizing a solution. In the milling or micronizing of crystals, care should be taken to avoid changing crystallinity from the desired crystalline form (i.e., changing to an amorphous or other polymorphic form).

A cooled crystallization mixture may be filtered under vacuum and the isolated solid product may be washed with a suitable solvent, such as, for example, cold recrystallization solvent. After being washed, the product may be dried under a nitrogen or air purge to afford the desired crystalline form. The product may be analyzed by a suitable spectroscopic or analytical technique including, but not limited to, for example, differential scanning calorimetry (DSC); X-ray powder diffraction (XRD); and thermogravimetric analysis (TGA) to assure the crystalline form of the compound has been formed. The resulted crystalline form may be obtained in an amount greater than about 70 wt. % isolated yield, based on the weight of the compound originally employed in the crystallization procedure, and preferably greater than about 90 wt. % isolated yield.

The feature and advantages of this invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of this disclosure that are, for brevity reasons, described in the context of a single embodiment, may also be combined so as to form sub-combinations thereof.

The invention is further illustrated by the following examples, which are not to be construed as limiting the invention in scope or spirit to the specific procedures described in them.

$^1$H NMR spectra were recorded with a Bruker 400 MHz or 600 MHz spectrometer at ambient temperature. Solid-state $^{13}$C NMR spectra were recorded with a Bruker 100 MHz spectrometer at ambient temperature (from about 21 to about 25° C.) using TMS (0 ppm) as the reference standard. $^1$H NMR spectra were obtained as CDCl$_3$, DMSO-d$_6$, CD$_3$OD or d$_6$-acetone solutions (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants J, when given, are reported in Hertz (Hz).

Low-resolution mass spectral (MS) data were generally determined on an Agilent 6120 Quadrupole HPLC-MS (Zorbax SB-C18, 2.1×30 mm, 3.5 micron, 6 minutes run, 0.6 mL/min flow rate, 5% to 95% (0.1% formic acid in CH$_3$CN) in (0.1% formic acid in H$_2$O)) with UV detection at 210 nm/254 nm and electrospray ionization mode (ESI).

EXAMPLES

The starting material N-(3-fluoro-4-((7-(2-hydroxy-2-methylpropoxy)quinolin-4-yl)oxy)phenyl)-1,5-dimethyl-3-oxo-2-phenyl-2,3-dihydro-1H-pyrazole-4-carboxamide can be prepared according to WO 2012118632 A1, the content of which is incorporated herein by reference in its entirety.

Example 1

Preparation of N-(3-fluoro-4-((7-(2-hydroxy-2-methylpropoxy)quinolin-4-yl)oxy)phenyl)-1,5-dimethyl-3-oxo-2-phenyl-2,3-dihydro-1H-pyrazole e-4-carboxamide p-toluenesulfonic acid Crystalline Form C N-(3-fluoro-4-((7-(2-hydroxy-2-methylpropoxy)quinolin-4-yl)oxy)phenyl)-1,5-dimethyl-3-oxo-2-phenyl-2,3-dihydro-1H-pyrazole-4-carboxamide (1.0 g, 1.80 mmol) was dissolved in methanol (30 mL) and dichloromethane (15 mL). A solution of 4-methylbenzenesulfonic acid hydrate (360 mg, 1.88 mmol) in methanol (2 mL) was added slowly. After stirring at ambient temperature for 1 hour, the solvent was removed to obtain a light yellow oil, which was crystallized in methanol (20 mL) at 20° C. to get the title compound as a white solid (1.26 g, 96%).

Solid-state $^{13}$CNMR (101 MHz) Peaks δ (ppm): 167.64, 164.19, 160.94, 154.29, 153.10, 148.14, 143.69, 141.50, 133.53, 130.18, 129.05, 127.25, 124.80, 114.78, 107.19, 100.84, 98.55, 96.78, 76.79, 70.95, 31.86, 29.15, 27.06, 21.98, 9.17.

Characterization of Crystalline Form C of Compound (I)

1. X-ray Powder Diffraction Study for Crystalline Form C of Compound (I)

The X-ray powder diffraction (XRPD) pattern was collected on an X-ray powder diffractometer (Empyrean, PANalytical, Holland) with an automatic transmission-reflection sample holder (3*15). The X-ray tube (Cu, kα, Kα1 (Å): 1.540598; Kα2 (Å): 1.544426; Kα2/Kα1=0.50) is set to voltage at 45 kV and current at 40 mA, irradiated length=10.0 mm. The scanning parameters were: continuous scan; range 3° to 40° (2θ±0.2°); step size 0.0168°; time per step 10 second. Data were collected at ambient temperature (from about 18 to about 30° C.). Sample (usually 1~2 mg) was prepared as flat plate specimens by slightly pressed on a glass slide to obtain a flat surface. The data were collected by Data Collector software, and analyzed by Data Viewer and HighScore Plus software. The XRPD pattern for Compound (I), Form C is shown in FIG. 1 and peaks and their related intensities in the XRPD pattern are shown in Table 1 below.

TABLE 1

Peaks in the XRPD pattern for Compound (I), Form C

| Degrees [°2θ] | d-spacing [Å] | Rel. Int. [%] | degrees [°2θ] | d-spacing [Å] | Rel. Int. [%] |
|---|---|---|---|---|---|
| 7.2008 | 12.26646 | 33.95 | 8.699 | 10.16997 | 4.35 |
| 9.890 | 8.93637 | 19.61 | 10.0589 | 8.78661 | 32.68 |
| 10.415 | 8.48672 | 7.91 | 12.639 | 6.99803 | 8.98 |
| 13.360 | 6.62179 | 12.32 | 14.029 | 6.30790 | 6.55 |
| 14.403 | 6.14486 | 6.48 | 14.9561 | 5.91872 | 25.06 |
| 15.670 | 5.65081 | 2.79 | 16.607 | 5.33372 | 21.26 |
| 16.764 | 5.28426 | 24.15 | 17.3955 | 5.09384 | 63.98 |
| 17.7478 | 4.99349 | 57.18 | 18.262 | 4.85406 | 25.07 |
| 18.6491 | 4.75414 | 54.82 | 19.031 | 4.65962 | 16.10 |
| 19.4756 | 4.55423 | 67.60 | 20.1337 | 4.40681 | 100.00 |
| 20.570 | 4.31428 | 8.40 | 20.901 | 4.24665 | 17.93 |
| 21.706 | 4.09098 | 22.92 | 22.329 | 3.9783 | 9.37 |
| 22.694 | 3.91516 | 20.16 | 23.365 | 3.80413 | 34.57 |
| 23.743 | 3.74437 | 6.39 | 23.96 | 3.71157 | 4.87 |
| 24.404 | 3.64455 | 43.59 | 24.513 | 3.62857 | 12.33 |
| 25.5249 | 3.48695 | 47.36 | 25.995 | 3.42489 | 14.94 |
| 26.287 | 3.38750 | 20.20 | 26.891 | 3.31278 | 7.84 |
| 27.721 | 3.21552 | 12.93 | 28.4051 | 3.13959 | 57.81 |
| 28.930 | 3.08378 | 8.62 | 29.618 | 3.01367 | 7.51 |
| 30.149 | 2.96185 | 8.30 | 30.460 | 2.93232 | 9.32 |
| 31.100 | 2.87340 | 7.25 | 31.657 | 2.82413 | 6.29 |
| 32.265 | 2.77227 | 5.14 | 32.627 | 2.74230 | 3.88 |
| 33.196 | 2.69657 | 7.12 | 33.670 | 2.65971 | 4.86 |
| 34.32 | 2.61114 | 2.48 | 34.792 | 2.57649 | 5.32 |
| 35.294 | 2.54096 | 5.89 | 36.621 | 2.45191 | 4.59 |

2. DSC of Crystalline Form C of Compound (I)

All DSC measurements were performed on a TA Instruments™ model Q2000 differential scanning calorimeter. The sample (about 2~6 mg) was weighted in an aluminum pan and recorded to a hundredth of a milligram, and transfer to the DSC instrument. The instrument was purged with nitrogen gas at 50 mL/min. Data were collected between room temperature and 300° C. at the heating rate of 10° C./min. The data was analyzed by TA Universal Analysis software.

3. TGA of Crystalline Form C of Compound (I)

All TGA scans were performed on TGA TA Q500 thermogravimetric analyzer. The sample (about 10~30 mg) was placed in a platinum pan pre-tared. The weight of the sample was measured accurately and recorded to a thousandth of a milligram by the instrument. The furnace was purged with nitrogen gas at 60 mL/min. Data were collected between room temperature and 300° C. at the hating rate of 10° C./min. The data was analyzed by TA Universal Analysis software.

4. Stability Test

A sample of crystalline form C of compound (I) (100~200 mg) was placed on a watching glass in the form of a thin layer (thickness ≤5 mm). The samples were exposed to the following conditions: high temperature (60±2° C.) for 10 days; high humidity (25±2° C., 90%±5% relative humidity) for 10 days; illumination condition (visible light 4500 lx±500 lx with ultraviolet light not lower than 0.7 W·h/m$^2$, 25±2° C., 60%±5% relative humidity) for 10 days; and room temperature (30±2° C., 65%±5% relative humidity) for 10 days, respectively. The impurity contents in the samples were determined at different time points (0, 5 and 10 days) by high performance liquid chromatography (HPLC), and the absorption peaks were normalized relative to the highest peak (corresponds to compound I) which is set to 100%. The instrument and conditions for HPLC are showed in Table 2 and the data are shown in Table 3.

TABLE 2

| Instrument and reagent | Instrument: Agilent 1200 or 1260, One over one hundred thousand of electronic balance, Volumetric flask, 0.45 μm nylon membrane filter; Reagent: Acetonitrile (HPLC), Monopotassium phosphate (AR), Potassium hydroxide (AR), Water (Millipore). |
|---|---|
| Solution Preparation | Blank Solution/Diluent: Mix acetonitrile and water at the ratio of 45/55 (v/v); Sample Solution: Transfer about 33 mg of crystalline form C of compound (I), accurately weighed, to a 100 mL volumetric flask and add diluent to dissolve. Dilute to volume with Diluent and mix well. |
| Chromatographic Conditions | Column: Octadecyl silane bonded silica gel column, 4.6 × 150 mm, 5 μm; Column temperature: 30° C.; Detection wavelength: 235 nm; Flow rate: 1.0 mL/min; Injection volume: 20 μL; Buffer solution: Dissolve 1.361 g of monopotassium phosphate in 1 L of water and mix well. Adjust with potassium hydroxide to a pH of 6.0. Filter the solution and sonicate to obtain buffer Solution; Mobile Phase: Mix Buffer and acetonitrile at the ratio of 55/45 (v/v); Run time: 30 min. |

TABLE 3

| | | The impurity contents | | |
|---|---|---|---|---|
| | Condition | 0 day | 5 days | 10 days |
| Form C | high temperature | 2.00% | 1.97% | 1.89% |
| | high humidity | 2.00% | 1.94% | 1.92% |
| | illuminating condition | 2.00% | 1.97% | 2.14% |
| | room temperature | 2.00% | 1.90% | 1.91% |
| Amorphous | high temperature | 0.14% | 0.13% | 0.10% |
| | high humidity | 0.14% | 0.11% | 0.07% |
| | illuminating condition | 0.14% | 0.36% | 0.56% |
| | room temperature | 0.14% | 0.07% | 0.07% |

The results in Table 3 indicate that crystalline form C of Compound (I) and amorphous compound (I) were stable for at least 10 days under the condition of high temperature, high humidity and at room temperature. The impurity contents in crystalline form C of Compound (I) and amorphous Compound (I) form increased 0.14% and 0.42%, respectively, when illuminating the samples for 10 days.

5. Hygroscopicity Test

A glass weighing bottle equipped with a stopper was tarred and the weight was recorded as $m_1$. Compound (I) in crystalline form C or amorphous form (about 1.0 g) was placed in the tared weighing bottle and capped with the stopper. The total weight was then recorded as $m_2$. The weighing bottle (without its stopper) was placed in a desiccator containing a saturated solution of ammonium chloride (80%±2% RH (relative humidity)) at 25±1° C. The weighing bottle capped with its stopper was weighed on day 5 and day 10 and the weight was recorded as $m_3$. The hygroscopic capacity was calculate according to the following formula and the results are listed in Table 4.

$$\text{(Hygroscopic capacity)} = \frac{m3 - m2}{m2 - m1} \times 100\%$$

TABLE 4

| Standing time | Hygroscopic capacity % (90% ± 5% RH) | |
|---|---|---|
| | Form C | amorphous |
| 5 d | 0.22 | 7.74 |
| 10 d | 0.43 | 8.48 |

The results from the Table 4 indicate that the crystalline form C of compound (I) was not hygroscopic whereas amorphous Compound (I) was hygroscopic.

6. Pharmacokinetics Test

The pharmacokinetic properties of amorphous Compound (I) or the crystalline form C of Compound (I) disclosed herein are assessed in beagle dogs. The LC/MS/MS system used in the analysis consists of an Agilent 1200 Series vacuum degasser, binary pump, well-plate autosampler, thermostatted column compartment, the Agilent G6430 Triple Quadrupole Mass Spectrometer with an electrosprayionization (ESI) source. Quantitative analysis was carried out using MRM mode. The parameters for MRM transitions are in the Table A.

TABLE A

| MRM | 490.2→383.1 |
|---|---|
| Fragmentor | 230 V |
| CE | 55 V |
| Drying Gas Temp | 350° C. |
| Nebulize | 0.28 MPa |
| Drying Gas Flow | 10 L/min |

An Agilent XDB-C18, 2.1×30 mm, 3.5 µM column was used for the analysis. 5 µL of the samples were injected. Analysis condition: The mobile phase was 0.1% formic acid in water (A) and 0.1% formic acid in methanol (B). The flow rate was 0.4 mL/min. And the gradient of Mobile phase was in the Table B.

TABLE B

| Time | Gradient of Mobile Phase B |
|---|---|
| 0.5 min | 5% |
| 1.0 min | 95% |
| 2.2 min | 95% |
| 2.3 min | 5% |
| 5.0 min | stop |

Alternatively, an Agilent 6330 series LC/MS/MS spectrometer equipped with G1312A binary pumps, a G1367A autosampler and a G1314C UV detector were used in the analysis. An ESI source was used on the LC/MS/MS spectrometer. The analysis was done in positive ion mode as appropriate and the MRM transition for each analyte was optimized using standard solution. A Capcell MP-C18 100× 4.6 mm I.D., 5 µM column (Phenomenex, Torrance, Calif., USA) was used during the analysis. The mobile phase was 5 mM ammonia acetate, 0.1% MeOH in water (A): 5 mM ammonia acetate, 0.1% MeOH in acetonitrile (B) (70/30, v/v). The flow rate was 0.6 mL/min. Column was maintained at ambient temperature. 20 µL of the samples were injected.

The capsule of the crystalline form C or the amorphous of Compound (I) mixed with adjuvants respectively was administered by gavage to beagle dogs in a dose of 7 or 10 mg/kg. The blood samples (0.3 mL) were drawn at 0.25, 0.5, 1.0, 2.0, 3.0, 4.0, 6.0, 8.0, 12 and 24 hour time points or 0.083, 0.25, 0.5, 1.0, 2.0, 4.0, 6.0, 8.0 and 24 hour time points and centrifuged at 3,000 or 4000 rpm for 2 to 10 min. The plasma solutions were collected, and analyzed by LC/MS/MS as described above. The pharmacokinetic parameters were calculated according to non-compartment model using WinNonlin procedure. The pharmacokinetic parameters are shown in Table 5.

TABLE 5

| | Pharmacokinetic profiles in beagle dogs | | | | | | |
|---|---|---|---|---|---|---|---|
| Example | Grain size D90 (µm) | Dose (mg/kg) | $T_{1/2}$ (h) | $T_{max}$ (h) | $C_{max}$ (ng/mL) | $AUC_{0\text{-}24h}$ (ng·h/mL) | $AUC_{0\text{-}\infty}$ (ng·h/mL) |
| Form C | 14 | 9.9 | 14.60 | 4.00 | 4755 | 59718 | 90052 |
| Amorphous | 32 | 9.7 | 15.05 | 3.33 | 2644 | 37282 | 55339 |

The results listed in Table 5 above show that the values of $C_{max}$, $AUC_{0\text{-}24h}$ and $AUC_{0\text{-}\infty}$ of crystalline form C of Compound (I) are much larger than the amorphous Compound (I), which indicates that the crystalline form C of Compound (I) has a good exposure and bioavailability in vivo in beagle dogs.

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A crystalline form of a compound of formula (I):

(I)

wherein the crystalline form is form C having:
a) an X-ray powder diffraction pattern comprising peaks, in terms of 2θ, at about 7.20°, about 10.06°, about 17.40°, about 17.75°, about 18.65°, about 19.48° and about 20.13°; or
b) an X-ray powder diffraction pattern comprising peaks, in terms of 2θ, at 7.20°±0.2°, 10.06°±0.2°, 17.40°±0.2°, 17.75°±0.2°, 18.65°±0.2°, 19.48°±0.2° and 20.13°±0.2°.

2. The crystalline form of claim 1 having an X-ray powder diffraction pattern comprising peaks, in terms of 2θ, at about 7.20°, about 10.06°, about 14.96°, about 16.76, about 17.40°, about 17.75°, about 18.65°, about 19.48°, about 20.13°, about 20.90°, about 21.71°, about 22.69°, about 23.37°, about 24.40°, about 25.52°, about 26.29° and about 28.41°; or at 7.20°±0.2°, 10.06°±0.2°, 14.96±0.2°, 16.76±0.2°, 17.40°±0.2°, 17.75°±0.2°, 18.65°±0.2°, 19.48°±0.2°, 20.13°±0.2°, 20.90°±0.2°, 21.71°±0.2°, 22.69°±0.2°, 23.37°±0.2°, 24.40°±0.2°, 25.52°±0.2°, 26.29°±0.2° and 28.41°±0.2°.

3. The crystalline form of claim 1, wherein the X-ray powder diffraction pattern is substantially in accordance with that shown in FIG. 1.

4. The crystalline form of claim 1, wherein the crystalline form is substantially pure.

5. A pharmaceutical composition comprising the crystalline form of claim 1 and a pharmaceutically acceptable excipient, carrier, vehicle or a combination thereof.

6. The pharmaceutical composition of claim 5 further comprising a therapeutic agent.

7. The pharmaceutical composition of claim 6, wherein the therapeutic agent is melphalan, cyclophosphamide, ifosfamide, busulfan, carmustine, lomustine, streptozocin, cisplatin, carboplatin, oxaliplatin, dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, topotecan, irinotecan, etoposide, trabectedin, dactinomycin, doxorubicin, epirubicin, daunorubicin, mitoxantrone, bleomycin, mitomycin, ixabepilone, tamoxifen, flutamide, gonadorelin analogues, megestrol, prednisone, dexamethasone, methylprednisolone, thalidomide, interferon alfa, leucovorin, sirolimus, temsirolimus, everolimus, afatinib, alisertib, amuvatinib, apatinib, axitinib, bosutinib, bortezomib, brivanib, cediranib, cabozantinib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, neratinib, nilotinib, niraparib, oprozomib, olaparib, pazopanib, pegaptanib, pictilisib, ponatinib, quizartinib, radotinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, vemurafenib, vismodegib, volasertib, alemtuzumab, bevacizumab, brentuximabvedotin, catumaxomab, cetuximab, denosumab, gemtuzumab, ipilimumab, nimotuzumab, ofatumumab, panitumumab, ramucirumab, rituximab, tositumomab, trastuzumab, idelalisib, duvelisib, gilteritinib, buparlisib, taselisib, copanlisib, voxtalisib, pilaralisib, sonolisib, perifosine, alectinib, ibrutinib, pertuzumab, nintedanib, cobimetinib, temsirolimus, sirolimus, pixantrone or a combination thereof.

* * * * *